United States Patent
Carlucci et al.

(10) Patent No.: US 7,635,797 B2
(45) Date of Patent: Dec. 22, 2009

(54) ABSORBENT ARTICLES FOR FEMININE PROTECTION WITH GEL-FORMING POLYSACCHARIDE-COMPRISING WINGS

(75) Inventors: Giovanni Carlucci, Chieti (IT); Antonella Pesce, Pescara (IT); Achille Di Cintio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 1036 days.

(21) Appl. No.: 10/265,802

(22) Filed: Oct. 7, 2002

(65) Prior Publication Data

US 2003/0068944 A1 Apr. 10, 2003

(30) Foreign Application Priority Data

Oct. 8, 2001 (EP) .................. 01123974

(51) Int. Cl.
*A61F 13/15* (2006.01)
(52) U.S. Cl. .................. 604/360; 604/367; 604/385.04
(58) Field of Classification Search ................ 604/360, 604/367, 374, 385.04
See application file for complete search history.

(56) References Cited

U.S. PATENT DOCUMENTS

| | | | |
|---|---|---|---|
| 5,275,591 A * | 1/1994 | Mavinkurve | ................ 604/387 |
| 5,769,833 A | 6/1998 | Hasse | |
| 5,954,705 A * | 9/1999 | Sawaki et al. | ......... 604/385.101 |
| 6,093,386 A * | 7/2000 | Sampino et al. | ................ 424/73 |
| 6,120,488 A * | 9/2000 | VanRijswijck et al. | . 604/385.28 |
| 6,261,679 B1 | 7/2001 | Chen et al. | |
| 6,287,581 B1 * | 9/2001 | Krzysik et al. | ............... 424/402 |
| 6,580,014 B1 | 6/2003 | Kasai et al. | |
| 6,603,054 B2 | 8/2003 | Chen et al. | |
| 2003/0220039 A1 | 11/2003 | Chen et al. | |
| 2005/0124799 A1 * | 6/2005 | Pesce et al. | ................... 536/20 |

FOREIGN PATENT DOCUMENTS

| | | |
|---|---|---|
| CN | 1156582 A | 2/1996 |
| EP | 1149597 A1 | 10/2001 |
| JP | 08-89530 | 4/1996 |
| JP | 08-173478 | 7/1996 |
| JP | 11347067 A | 6/1998 |
| WO | WO 92/09636 A1 | 6/1992 |
| WO | WO 97/36563 A1 | 10/1997 |
| WO | WO 98/26808 | 6/1998 |

* cited by examiner

*Primary Examiner*—Tatyana Zalukaeva
*Assistant Examiner*—Lynne Anderson
(74) *Attorney, Agent, or Firm*—Amanda T. Barry; James E. Oehlenschlager; Kevin C. Johnson

(57) ABSTRACT

The present invention relates to absorbent articles, in particular sanitary napkins and panty liners, which offer improved protection and comfort to the wearer by having side panels, so-called wings, which comprise a gel-forming polysaccharide, preferably a chitosan material.

7 Claims, No Drawings

ABSORBENT ARTICLES FOR FEMININE PROTECTION WITH GEL-FORMING POLYSACCHARIDE-COMPRISING WINGS

FIELD OF THE INVENTION

The present invention relates to absorbent articles for feminine protection, in particular sanitary napkins and panty liners, which offer improved protection and comfort to the wearer by having side panels, so-called wings, which comprise a gel-forming polysaccharide, preferably a chitosan material.

BACKGROUND OF THE INVENTION

An increasingly important consumer need, which underlies development in the field of sanitary absorbent article, in particular catamenials, is the provision of products with higher protection and comfort level during use.

Numerous developments in the area of absorbent articles address a great variety of different consumer needs associated with sanitary absorbent articles.

For example, to overcome side leakage occurrence absorbent articles have typically been provided with so-called side panels or wings, which are also used for securely attaching them to the wearer's undergarment in the crotch region. Improved protection, in particular the prevention of so-called run-off of discharged body fluids from the topsheet along the longitudinal edges of the article in the crotch region, before these fluids have been absorbed by the absorbent core of the article, is a key priority. Side leakage, although drastically reduced by absorbent articles with wings compared to absorbent articles without wings, still occurs in some instances, such as heavy flow during a women's period or in the course of sport activities. Thus, there is a need to further decrease side leakage occurrence.

Women who have particular sensitive skin might not consider using absorbent articles with wings. Due to the construction of such articles, a certain friction might result between portions of those wings and the inner side of the wearer's thighs, especially when the wearer is walking. As a result, skin sensitiveness might be observed.

The present invention provides significant improvements in both above areas by the incorporation of gel-forming polysaccharides, in particular chitosan materials, into the wings. Advantageously, both problems are overcome by the use of the same ingredient.

BACKGROUND OF THE INVENTION

Articles comprising chitosan materials are known from the art. For example, WO99/32697 discloses that chitosan and chitin-based polymers exhibit increased antimicrobial activity when coated onto the surface of a hydrophobic material such as polypropylene. The use of chitosan as absorbent material for use in absorbent core structures of absorbent articles is suggested in EP 627225, WO 99/32697, WO 96/20015, EP 566118, WO 95/11925 and WO 99/26670.

None of these prior art references has addressed or even recognized the need for providing absorbent articles with wings offering improved protection and comfort to the wearer in the wing regions of the article.

SUMMARY OF THE INVENTION

The present invention relates to absorbent articles, in particular sanitary napkins and panty liners, which offer improved protection and comfort to the wearer by having side panels, so-called wings, which comprise a gel-forming polysaccharide, preferably a chitosan material.

DETAILED DESCRIPTION OF THE INVENTION

The term 'longitudinal' as used herein refers to the direction of the central longitudinal axis of the central absorbent pad of the absorbent article of the present invention. The term 'transverse' as used herein refers to the direction of the transverse axis, which is generally perpendicular to the longitudinal axis, of the central absorbent pad of the absorbent article of the present invention.

The term 'absorbent article' is used herein in a very broad sense, including any article suitable for feminine protection, being able to receive and/or absorb and/or contain and/or retain body fluids.

The absorbent article of the present invention comprises a central absorbent pad having a longitudinal axis and a transverse axis, longitudinal edges extending in a generally longitudinal direction and transverse ends extending in a generally transverse direction. The central absorbent pad of the absorbent article, which is referred to in the present invention, typically comprises a structure having a fluid pervious topsheet as the wearer-facing layer, a fluid impervious backsheet that is preferably water vapour and/or gas pervious as the garment-facing layer and an absorbent core element comprised there between. Particularly preferred absorbent articles in the context of the present invention are disposable absorbent articles. The absorbent article of the present invention has at least one pair of wings for securely attaching the article in the crotch region of the wearer's garment. Preferred disposable absorbent articles according to the present invention are disposable absorbent articles for feminine protection like incontinence pads, sanitary napkins or panty liners.

The term 'disposable' is used herein to describe absorbent articles, which are not intended to be laundered or otherwise restored or reused as an article (i.e. they are intended to be discarded after a single use and preferably to be recycled, composted or otherwise disposed of in an environmentally compatible manner).

The term 'use', as used herein, refers to the period of time that starts when the absorbent article is actually put in contact with the anatomy of the user.

By 'body fluid' it is meant herein any fluid produced by human body including for instance perspiration, urine, menstrual fluids, vaginal secretions and the like.

The present invention relates to absorbent articles with wings, such as sanitary napkins or panty liners, which offer improved protection and comfort to the wearer in the wing regions.

By 'wings' it is meant hereinafter elements of the absorbent article extending from the longitudinal edges of the absorbent article. Said wings have an in-use folded configuration and an unfolded configuration and can have any suitable size and shape. Preferably, said wings can comprise an attachment system for attaching them onto the wearer's garment, such as an adhesive coating or a mechanical fastening system like Velcro®. The wings of the absorbent article according to the present invention comprise a gel-forming polysaccharide. It is particularly preferred that said gel-forming polysaccharide is present from about 20% to about 100% of the surface of the wings, which is facing the wearer's skin in the in-use folded configuration. This means in particular that the chitosan material is preferably located on and around the folding axis, which is generated when the wings are folded through the leg openings of the wearer's garment over the crotch area of this garment.

The wording 'in-use folded configuration' conventionally refers to the in-use configuration, in which the absorbent article is firmly placed in the inner crotch portion of an undergarment, such that the wings are folded around the crotch portion through the leg openings, so as to overlie the outer crotch portion of the undergarment and are secured in such a position. More generally, the wording 'in-use folded configuration' refers to the configuration of an absorbent article, in which the wings are folded along a line delimiting the absorbent core and the wings onto the garment facing side of the article. In case the delimiting line is not linear, the closest possible fold along the delimiting line should be used instead. As used herein, the term 'unfolded configuration' or 'non-folded configuration' refers to the configuration in which the wings of the absorbent article are in the same plane as the remaining of the absorbent article.

The wings can be made of any suitable material. They can be integral extensions of one, some or all of the materials used to provide the central absorbent pad. Alternatively, the wings can be constructed separately from the absorbent central pad. In this case they can be made from the same materials used already for the absorbent pad or form different materials such as those mentioned herein already. If provided separately, the wings are attached to the central absorbent pad by any means conventionally used in combining absorbent articles, such as adhesives, thermo or mechanical bonding. A key benefit of the integral construction is the ease of manufacture while the attached wings provide benefits in material consumption and flexibility in material selection for the article manufacturer.

In an embodiment according to the present invention, the wings comprise a top sheet, a backsheet and optionally also comprise an absorbent core. In a preferred embodiment, the wing topsheet is also integral with the material that is used for topsheet. In another preferred embodiment the wing back sheet is also integral with the material that is used for backsheet. In a preferred embodiment for use as a thong shaped sanitary napkin, no absorbent material or only a very thin absorbent material such as a tissue is provided as absorbent material in the wings.

Wings can be essentially of any shape as long as at least one wing overlaps the central longitudinal axis of the absorbent article when in the in-use folded configuration. The wings may have the same shape but be located at different locations along the longitudinal edges such that they do not overlap when in the in use folded configuration. The wings may have a different shape to achieve this purpose. Any differing shapes between the wings may be used provided they do not overlap in the in use folded configuration. Wings may be different shapes and be located at different distances along the longitudinal edges. The wings can extend along a small or a long portion of the central absorbent pad. It is preferred that the wings be as long as practical to maximize the extent of undergarment side edge that is covered. In this respect, it is possible and preferred that one or even both wings extend all the way to the rear end of the absorbent article.

As the skilled person will acknowledge, the body-facing surface of the wings is in most cases similar or even essentially identical with the so-called topsheet of the article, which forms the body-contacting surface the article. Such topsheets are usually apertured formed films or nonwoven structures, which are compliant, soft feeling and non-irritating to the wearer's skin. However, when wings are incorporated into the article, the topsheet material is not only in a substantially static contact with the wearer's skin, as it is the case for the topsheet itself. At the same time, in case of the body-contacting surface of the wings, said topsheet material is also in a dynamic contact with the wearer's skin, because when the wearer e.g. walks, the inner side of the wearer's thighs will move along a portion of the body-facing surface of the wings, which are folded over the wearer's garment, usually in the crotch region. By this, a certain amount of friction is generated between the wings and the wearer's thighs, which can lead to increased sensitiveness on the epidermis of the wearer's skin.

Another negative associated with commercially available absorbent articles with wings is so-called run-off leakage from the topsheet along the peripheral, especially the longitudinal, edge of the article, especially in occurrence of heavy flow or movement.

It has now been found that both above areas of protection can be successfully addressed by providing an absorbent article with wings, wherein said wings comprise a gel-forming polysaccharide preferably on the skin-contacting surface of the wings. The gel-forming polysaccharides for use in the present invention have the ability to form a gel with aqueous body exudates, such as blood, menses, vaginal fluids, perspiration or other body fluids. Due to this, a gel layer is generated on the contact surfaces of the wings with the wearer's skin. Thus, a skin contact surface with significantly lower friction between the wing's surface and the skin is generated, which results in improved skin compatibility and reduced instances of skin irritations and rash. On the other hand, run-off of body fluids from the topsheet of the article along the longitudinal edges of the article in the crotch region, where those wings are usually extending from the longitudinal edge of the central pad of the absorbent article for attachment onto the user's undergarment according to the present invention, is reduced or even prevented by gelifying those body fluids.

The absorbent article of the present invention comprises as an essential feature at least a 'gel-forming polysaccharide' or mixture thereof in the wings. Gel-forming polysaccharides for use herein have the ability, when exposed to aqueous fluids, to react with components of those fluids, e.g. water, and based on the amount of those components this reaction will result in viscosity increase of those fluids or even gel formation. This effect is often referred to as "thickening" of aqueous fluids. Suitable gel-forming polysaccharides for use according to the present invention include but are not limited to pectin, agar-agar, guar gum, gum arabicum, gellan gum, scleroglucan, xanthan, κ-carrageenan, glucomannan, sodium alginate, propylene glycol alginate, carboxymethyl cellulose, chitin and chitosan materials like chitosan, modified chitosan, cross-linked chitosan and chitosan salts.

Chitosan materials are preferred herein as they have proven to be particularly useful, as they have the ability to instantaneously reduce fluid diffusion once they are contacted with bodily fluids; thereby concentrating acquired fluid in their close proximity. This reduction of internal liquid transport results in reduced surface area of the absorbed fluid.

The above benefits are obtained due to the properties of chitosan material to instantaneously gelify bodily fluids encountering it. The gelification rate of chitosan material is only a few seconds towards bodily fluids, i.e., physiological fluids like menses. Without wishing to be bound by any theory, it is believed that chitosan materials provide fluid absorption/gelification by multiple mechanisms.

Firstly, the fluid absorption and retention characteristics of chitosan materials due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., —NH$_3^+$ $^+$H$_3$N—) and thus repel one another. This leads to expansion of the polymer structure, which, in turn permits absorption of molecules. This mechanism can continue until the limits of molecular tension are reached.

Secondly, the positively charged cationic groups of the chitosan materials will interact with negatively charged anionic group-bearing molecules present in bodily fluids, like the carboxylic groups of proteins or hydroxylic acid bearing entities like short chain acid (e.g., butyric acid) and thus forms three-dimensional network, which will entrap most molecules (like lipids, acids) thereby retaining fluid. This rapid physical change of the bodily fluid will instantaneously immobilize it in the article avoiding fluid transfer.

Advantageously, the use of chitosan material is compatible with skin safety. Indeed, the cationic properties of chitosan materials allow binding to the negatively charged surface of the skin, typically in the case of perspiration occurrence thereby moisturizing the skin and providing a long lasting softness and fullness.

Another advantage of chitosan materials in the context of the present invention is their antimicrobial activity. Thanks to this, microbes are hindered to grow in regions with high potential of skin irritations and rash.

Chitosan Materials

By 'chitosan material' it is meant herein chitosans, modified chitosans, crosslinked chitosans, chitosan salts and any suitable mixture thereof.

Chitosan is a partially or fully deacetylated form of chitin, a naturally occurring polysaccharide. Indeed, chitosan is an aminopolysaccharide usually prepared by deacetylation of chitin (poly-beta(1,4)-N-acetyl-D-glucosamine).

The chitosan used herein is suitably in relatively pure form. Methods for the manufacture of pure chitosan are well known. Generally, chitin is milled into a powder and dematerialized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

Preferred chitosan materials for use herein have an average degree of deacetylation (D.A.) of more than 75%, preferably more than 80%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by titration, dye adsorption, UV-VIS, IR, and NMR spectroscopy.

Suitable chitosan materials to use herein include both water-soluble and water insoluble chitosan. As used herein, a material will be considered to be water-soluble when it substantially dissolves in excess water to form a clear and stable solution, thereby, losing its initially particulate form and becoming essentially molecularly dispersed throughout the water solution. Preferred chitosan materials for use herein are water soluble, i.e., at least 0.5 gram, preferably at least 1 gram and more preferably at least 2 grams of the chitosan materials are soluble in 100 grams of water at 25° C. and one atmosphere. By "solubility" of a given compound it is to be understood herein the amount of said compound solubilised in de-ionized water at 25° C. and one atmosphere in absence of precipitate.

As a general rule, the water-soluble chitosan materials will be free from a substantial degree of crosslinking, as crosslinking tends to render the chitosan materials water insoluble.

Water-soluble chitosan materials as defined herein are preferred as they have the benefit to be more active in terms of gelifying the bodily fluid. Indeed such water-soluble chitosan materials have the ability to absorb and/or electrostatically interfere with water molecules.

Chitosan materials (i.e., chitosan and -chitosan salts, modified chitosans and cross-linked chitosans) may generally have a wide range of molecular weights. Chitosan materials with a wide range of molecular weights are suitable for use in the present invention, typically chitosan materials for use herein have a molecular weight ranging from 1 000 to 10 000 000 grams per gram moles and more preferably from 2 000 to 1 000 000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa·s (1 centipoise) to about 80,000 mPa·s (80,000 centipoise), more suitably from about 30 mPa·s (30 centipoise) to about 10,000 mPa·s (10,000 centipoise), even more suitably from 50 mPa·s (50 centipoise) to about 1,000 mPa·s (1,000 centipoise) and most suitably from 100 mPa·s (100 centipoise) to about 500 mPa·s (500 centipoise).

The pH of chitosan materials depends on the preparation of the chitosan materials. Preferred chitosan materials for use herein have an acidic pH, typically in the range of 4 to 6, more preferably from 4 to 5.5 and even more preferably from 4.5 to 5.5. Highly preferred pH is around pH 5, which corresponds to the skin pH. By 'pH of chitosan material' it is meant herein the pH of a 1% chitosan solution (1 gram of chitosan material dissolved in 100 grams of distilled water) measured by pH-meter.

Chitosan materials with acidic pH are preferred herein as the cationic character of acidic chitosan materials will be increased and thus their fluid absorbing ability and gelifying ability. However too high acidity is detrimental to skin safety. Thus it is highly preferred herein to use chitosan materials with a pH in the range of 4.5 to 5.5, thereby delivering the best compromise between fluid handling/gelifying properties on one side and skin compatibility on the other side.

Particularly suitable chitosan materials for use herein are chitosan salts, especially water-soluble chitosan salts. A variety of acids can be used for forming chitosan salts. Suitable acids for use are soluble in water or partially soluble in water, are sufficiently acidic to form the ammonium salt of chitosan and yet not sufficiently acidic to cause hydrolysis of chitosan, and are present in amount sufficient to protonate the reactive sites of chitosan.

Preferred acids can be represented by the formula:

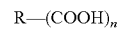

R—(COOH)$_n$ wherein n has a value of 1 or 2 or 3 and R represents a mono- or divalent organic radical composed of carbon, hydrogen and optionally at least one of oxygen, nitrogen and sulfur or R is simply a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any chitosan salts formed from the reaction of chitosan with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Highly preferred chitosan salts for use herein are those formed by the reaction of chitosan with an amino acid. Amino acids are molecules containing both an acidic and amino functional group. The use of amino acids instead of other acids is highly preferred as those chitosan amino salts have higher skin compatibility. Indeed most of the amino acids are naturally present on the skin. Chitosan salts of pyrrolidone carboxylic acid are effective moisturizing agents and are non-irritating to skin.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

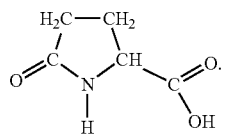

Highly preferred chitosan salts are chitosan pyroglutamate salt, which is a mixture of chitosan (a macromolecule) and pyroglutamic acid (independent monomers), chitosonium pyrrolidone carboxylate, which is the chitosan salt of 2-pyrrolidone-5-carboxylic acid. Reference is made to WO 98/07618, which describes in details processes for the preparation of such chitosan salts.

Other chitosan materials suitable for use herein include cross-linked chitosans and modified chitosans. Crosslinking agents suitable for use in the present invention are generally water-soluble and do not substantially reduce the gel-forming and antimicrobial properties of chitosan. One suitable crosslinking agent is an organic compound having at least two functional groups or functionalities capable of reacting with active groups located on the chitosan materials. Examples of such active groups include, but are not limited to, carboxylic acid (—COOH), amino (—$NH_2$), or hydroxyl (—OH) groups. Examples of such suitable crosslinking agents include, but are not limited to, diamines, polyamines, diols, polyols, polycarboxylic acids, polyoxides and the like. One way to introduce a crosslinking agent with the chitosan solution is to mix the crosslinking agent with chitosan during preparation of the solution. Another suitable crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$. Since the cations of chitosan possess antimicrobial properties, it is preferred herein to not use a crosslinking agent reacting to the cations, unless no alternative crosslinking agent is available.

In the embodiment herein where crosslinking agents are used, a suitable amount of crosslinking agent is from 0.001 to 30 weight percent based on the total dry weight of chitosan used to prepare the crosslinked-chitosan, more specifically from 0.02 to 20 weight percent, more specifically from 0.05 to 10 weight percent and most preferably from 0.1 to 5 weight percent.

Modified chitosans for use herein are any chitosan where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472. Water-soluble glycol chitosan and carboxymethyl chitosan are for instance described in WO87/07618.

Particularly suitable modified chitosans for use herein include water-soluble covalently bonded chitosan derivatives or ionically bonded chitosan derivatives obtained by contacting salt of chitosan with electrophilic organic reagents. Reference is made to EP-A-737 692, where such water-soluble chitosan derivatives are described.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation of more than 85%, a water solubility of 1% (1 gram is soluble in 100 grams of distilled water at 25° C. and one atmosphere), a pH of 4.5 and a viscosity between 100-300 cps. Chitosan pyrrolidone carboxylate is commercially available under the name Kytamer® PC from Amerchol Corporation.

Typically, the wings of the absorbent articles comprise gel-forming polysaccharide, preferably chitosan material, or a mixture thereof at a level of from 0.5 $g/m^2$ to 350 $g/m^2$, preferably from 1 to 100 $g/m^2$, more preferably from 3 $g/m^2$ to 80 $g/m^2$ and most preferably from 4 $g/m^2$ to 30 $g/m^2$. In a preferred embodiment, the gel-forming polysaccharide, preferably chitosan material, or mixture thereof covers from 20 to 100% of the in-use skin-facing surface of the wings at a loading of from 0.5 $g/m^2$ to 350 $g/m^2$, preferably from 1 $g/m^2$ to 100 $g/m^2$, more preferably from 3 $g/m^2$ to 800 $g/m^2$ and most preferably from 4 $g/m^2$ to 30 $g/m^2$.

Chitosan materials have the ability of instantaneously changing the physical properties of bodily fluids. Indeed a gelification of the bodily fluid is obtained when the fluid comes into contact with chitosan material. Chitosan material has the advantage of having a high gelification rate. This can be quantified by measuring the quantity and speed of wicking within the material. It is important to consider both the speed of transport and the quantity transported such that a value for the liquid transport would indicate quantity of liquid transported per time increment through a defined cross-section of the material. This can be measured for example against gravitational forces or for horizontal wicking.

Optional Components

According to the present invention, the wings of the absorbent articles can comprise as an optional component an absorbent gelling material (sometimes referred to as "supersorber").

Particularly preferred absorbent gelling materials for use herein are anionic absorbent gelling materials, i.e., absorbent gelling materials, which are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Generally, the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

The amount of absorbent gelling material particles used in the wings of the article according to the present invention, especially disposable absorbent articles, will typically range from 5 $g/m^2$ to 250 $g/m^2$, preferably from 7 $g/m^2$ to 150 $g/m^2$, more preferably from 10 $g/m^2$ to 100 $g/m^2$.

Adding anionic absorbent gelling material to the chitosan material is able to further enhance the advantages of the present invention. Indeed anionic absorbent gelling materials are believed to further enhance the cationic properties of chitosan materials. Without to be bound by any theory, it is believed that the negatively charged anionic groups of anionic absorbent gelling materials protonate the cationic groups of chitosan materials, thereby enhancing their cationic properties. This translates in improved gelification properties, especially further enhanced gelification rate.

Combining anionic absorbent gelling materials, namely synthetic anionic absorbent gelling materials as described herein (typically having a degree of neutralization of from 25% to 90%) together with chitosan materials in the wings of an absorbent article results in outstanding fluid absorption capacity not only towards water and especially towards electrolytes-containing solutions like menses. This is believed to be due to the reduction of the salt poisoning effect associated to the presence of chitosan materials beside anionic absorbent gelling material.

Furthermore, the use of anionic absorbent gelling materials, namely synthetic anionic absorbent gelling materials as described herein (typically having a degree of neutralization of from 25% to 90%) together with chitosan materials exhibits high gel strength during fluid absorption.

In a preferred embodiment of the present invention, the chitosan material and the anionic absorbent gelling material are present in the wings of the absorbent article at a weight ratio of chitosan material to absorbent gelling material of from 10:1 to 1:10, preferably from 5:1 to 1:5, more preferably from 3:1 to 1:3 and most preferably from 2:1 to 1:2. Within these ratio ranges, optimum performance on fluid handling is obtained.

The Absorbent Article

Preferred absorbent articles herein are pantiliners, sanitary napkins, incontinent pads and the like. The gel-forming polysaccharide, preferably chitosan material (and optional absorbent gelling material), may be incorporated into the wings at any locations and preferably into the in-use skin-facing surface of the wings of such articles by any of the methods known for such purpose by those skilled in the art. In a particularly preferred embodiment, the gel-forming polysaccharide is exclusively situated on the in-use skin-facing surface of the wings.

The chitosan material as described herein may be incorporated in particle form as a powder or granulate. When used in particle form the chitosan materials as described herein and the optional absorbent gelling material may be granulated separately and then mixed together or granulated together.

The chitosan material might also be applied onto the surface of the wings, which is facing the wearer's skin in the in-use folded configuration of the wings, by simply spraying a solution containing chitosan material and letting said layer to dry.

Preferably, at least a portion of the garment-facing side of the central pad of the absorbent article of the present invention is coated with a panty-fastening adhesive. This adhesive is intended to attach the central absorbent pad onto the crotch portion of the wearer's undergarment during use of this article. Any adhesive used in the art for such a purpose can be used herein, with pressure-sensitive adhesives being preferred. The adhesive-coated portion of the garment-facing side of the central pad is preferably covered by a suitable release liner.

EXAMPLES

To illustrate the present invention, an example was prepared starting from an absorbent article with wings, commercially available under the name Always®. A clear chitosan solution was prepared by dissolving 1 g of chitosonium pyrrolidone carboxylate, commercially available from Amerchol Corporation under the name Kytamer® PC, in 100 g of distilled water and stirring at 25° C. over 1 night. Then 10 g of the prepared solution were sprayed onto the whole surface of each wing, which is facing the wearer's skin in the folded in-use configuration.

What is claimed is:

1. Absorbent article suitable for feminine protection comprising a central absorbent pad having a body-facing side and a garment-facing side, a longitudinal axis and a transverse axis, longitudinal edges extending in a generally longitudinal direction and transverse ends extending in a general transverse direction, and said article comprises wings extending from said longitudinal edges of said central absorbent pad, said wings comprising a gel-forming polysaccharide that is chitosonium pyrrolidone carboxylate and/or chitosonium lactate, and wherein when said gel-forming polysaccharide is exposed to aqueous fluids having a viscosity said gel-forming polysaccharide increases the viscosity of said aqueous fluids.

2. An absorbent article according to claim 1, wherein said wings have an in-use folded configuration and a non-folded configuration, said wings further having a surface, which faces the skin of the wearer in the in-use folded configuration, said wings comprising said gel-forming polysaccharide on said surface, which faces the skin of the wearer in the in-use folded configuration.

3. An absorbent article according to claim 1, wherein an aqueous solution of said gel-forming polysaccharide is sprayed onto said surface of said wings, which faces the skin of the wearer in the in-use folded configuration.

4. An absorbent article according to claim 1, wherein said gel-forming polysaccharide is comprised in said wings at a level of from about 0.5 g/m² to about 500 g/m².

5. An absorbent article according to claim 1, wherein said gel-forming polysaccharide is present on said surface of said wings, which faces the skin of the wearer in the in-use folded configuration of said wings at a loading of from about 0.5 g/m² to about 350 g/m².

6. An absorbent article according to claim 1, wherein said gel-forming polysaccharide is selected from the group consisting of pectin, agar-agar, guar gum, gum arabicum, gellan gum, scleroglucan, xanthan, K-carrageenan, glucomannan, sodium alginate, propylene glycol alginate, carboxymethyl cellulose, chitin, and chitosan materials like chitosan, modified chitosan, cross-linked chitosan and/or a chitosan salt and mixtures thereof.

7. An absorbent article according to claim 1, wherein said gel-forming polysaccharide is chitosonium pyrrolidone carboxylate and/or chitosonium lactate.

* * * * *

UNITED STATES PATENT AND TRADEMARK OFFICE
CERTIFICATE OF CORRECTION

| | | |
|---|---|---|
| PATENT NO. | : 7,635,797 B2 | Page 1 of 1 |
| APPLICATION NO. | : 10/265802 | |
| DATED | : December 22, 2009 | |
| INVENTOR(S) | : Carlucci et al. | |

It is certified that error appears in the above-identified patent and that said Letters Patent is hereby corrected as shown below:

<u>Column 12 Claim 6</u>

Line 13, delete "K-carrageenan" and insert --κ-carrageenan--.

Signed and Sealed this

Sixteenth Day of March, 2010

David J. Kappos
*Director of the United States Patent and Trademark Office*